United States Patent
Kokuryo et al.

(10) Patent No.: US 7,050,949 B2
(45) Date of Patent: *May 23, 2006

(54) SIGNAL PROCESSING METHOD AND DEVICE

(75) Inventors: Kazuto Kokuryo, Otsu (JP); Shinji Nagao, Otsu (JP)

(73) Assignee: Niles Co., Ltd., Tokyo (JP)

( * ) Notice: Subject to any disclaimer, the term of this patent is extended or adjusted under 35 U.S.C. 154(b) by 383 days.

This patent is subject to a terminal disclaimer.

(21) Appl. No.: 10/412,738

(22) Filed: Apr. 11, 2003

(65) Prior Publication Data

US 2004/0080751 A1    Apr. 29, 2004

Related U.S. Application Data

(63) Continuation-in-part of application No. 09/748,434, filed on Dec. 26, 2000, now Pat. No. 6,590,662.

(30) Foreign Application Priority Data

Dec. 28, 1999    (JP)    ............................ 11-372504

(51) Int. Cl.
*H03F 1/26*    (2006.01)
*G01N 21/55*   (2006.01)
*G01N 21/85*   (2006.01)

(52) U.S. Cl. .................. 702/191; 356/445; 250/573

(58) Field of Classification Search ................ 356/445; 250/214 R, 214 C, 214.1, 215, 573, 574; 318/483; 340/602; 327/514; 702/189, 190, 702/191

See application file for complete search history.

(56) References Cited

U.S. PATENT DOCUMENTS

| | | | | |
|---|---|---|---|---|
| 3,947,131 A | * | 3/1976 | Karl ........................... 356/445 |
| 4,916,374 A | * | 4/1990 | Schierbeek et al. ......... 318/483 |
| 5,225,669 A | * | 7/1993 | Hasch et al. ................. 327/514 |
| 6,429,933 B1 | * | 8/2002 | Jackson, Jr. ............. 356/239.8 |
| 6,573,490 B1 | * | 6/2003 | Hochstein ................... 250/573 |
| 6,590,662 B1 | * | 7/2003 | Kokuryo et al. ............ 356/445 |
| 6,603,137 B1 | * | 8/2003 | Hochstein ................... 250/573 |

FOREIGN PATENT DOCUMENTS

| FR | 2787406 | 6/2002 |
|---|---|---|
| JP | 57-118952 | 7/1982 |
| JP | 2-68248 | 3/1990 |
| JP | 10-186059 | 7/1998 |

* cited by examiner

Primary Examiner—Layla G. Lauchman
Assistant Examiner—Juan D. Valentin, II
(74) Attorney, Agent, or Firm—Hamre, Schumann, Mueller & Larson, P.C.

(57) ABSTRACT

A signal processing method and a signal processing device are provided in which a signal obtained from an object as an input signal, a time lag signal is generated from the input signal, a difference between the input signal and the time lag signal, and the generation of the difference is detected, so that a portion of the object at a position where the difference is generated is featured.

30 Claims, 17 Drawing Sheets

| Input data | Data to be leveled | Shift-out data | Output data |
|---|---|---|---|
| Dn··· | [D8\|D7\|D6\|D5\|D4\|D3\|D2\|D1]<br>n | | → F(1) |
| Dn··· | [D9\|D8\|D7\|D6\|D5\|D4\|D3\|D2]<br>n | D1 | → F(2) |
| Dn··· | [D10\|D9\|D8\|D7\|D6\|D5\|D4\|D3]<br>n | D2 | → F(3) |

$$F(1) = (D1 + D2 + \cdots + Dn)/n$$

$$F(2) = (D2 + D3 + \cdots + D(n+1))/n$$

$$F(3) = (D3 + D4 + \cdots + D(n+2))/n$$

Fig.7

SIGNAL PROCESSING METHOD AND DEVICE

This application is a continuation-in-part of U.S. application Ser. No. 09/748,434, filed Dec. 26, 2000 now U.S. Pat. No. 6,590,662, which is incorporated by reference herein in its entirety.

BACKGROUND OF THE INVENTION

1. Field of the Invention

The present invention relates to a signal processing method and a device for the same. The signal processing method is useful for detecting liquid or the like adhering to a surface of a product being monitored.

2. Description of the Related Art

The following describe the prior art by referring to signal processing in a rain sensing method.

Conventionally, many types of rain sensors for vehicles have been developed. For example, a rain sensor employing an optical method as follows is known. A light emitted from a photo emission element (light emission element) is reflected on a sensing surface and the reflected light is received by a photo detector, and then a rain drop is sensed. That is, the reflection condition varies if an object such as a water drop exists on the sensing surface, and the amount of the detected light by the photo detector will decrease. A conventional rain sensor senses a rain drop by detecting this variation.

In the above mention detection, normally, a method for comparison with the reference value (threshold method) had been used (i.e. JP 10-186059 A).

In practical use of such a conventional rain sensor, the rain sensor will be used in various conditions, so that a means for preventing malfunction is necessary. In order to achieve this object, the conventional rain sensor uses plural reference values that are set according to the operation modes (JP 10-186059 A), or replaces and switches reference values one by one (JP 2-68248 A).

As mentioned above, with the conventional rain sensor, the logic for rain drop detection is complicated, and consequently, a high-speed processing for rain drop detection becomes difficult. In addition, in either of the above mentioned conventional methods, the rain drop is detected by the comparison with the reference value based on judging the status on the sensing surface. Therefore, the prevention the malfunction is difficult because of the influence of the light from the outside or the influence of the status of the sensing surface, e.g. where dirt is present.

Moreover, the photo emission element and the photo detector have a disadvantage that the element characteristic will vary when the temperature varies. Especially, the photo emission element such as LED has a characteristic that the output will decrease when the temperature rises. Due to this characteristic, such element has a problem that an appropriate detection cannot be processed unless data correction by monitoring and feeding back the output is processed.

For example, in JP 57-118952 A, a windshield wiper controller is disclosed. This apparatus employs a method in which a light emitted from a photo emission element and reflected on the surface of a windshield glass is received by a photo detector, then the amount of the rain drop is judged according to the received light signal level, and the windshield wiper is driven.

In more detail, the received light signal is detected, then the detected signal is provided to the differential circuit and pulse signals corresponding to the envelope of the received light signal are picked out, and these pulse signals are counted.

In this JP 57-118952 A, the detailed method of how to pick out the pulse signals is not clearly disclosed. However, judging from FIG. 3(c) of the publication, the system will pick out a pulse signal when detecting the intersection of the envelope and the threshold.

In short, in the technology disclosed in the JP 57-118952 A, a rain drop impacting the surface of the windshield may be detected and counted and the detection for impact of a rain drop is processed by comparison of the envelope with the threshold.

SUMMARY OF THE INVENTION

Therefore, with the foregoing in mind, an object of the present invention is to provide a signal processing method and a signal processing device that are capable of detecting a dynamic change in input signals without comparing an input signal with a reference value for judgment.

Another object of the present invention is to provide a signal processing method that is capable of accurate processing even if a level of an input signal varies due to temperature characteristics of a photo emission element and a photo detector.

The present invention is characterized by detecting a dynamic change itself in an input signal. In contrast, conventionally a change in an input signal is detected by comparison with a reference value.

To achieve the above-described object, a first signal processing method according to the present invention includes: receiving a signal obtained from an object as an input signal; generating a time lag signal from the input signal; calculating a difference between the input signal and the time lag signal; and detecting the generation of the difference so as to feature a portion of the object at a position where the difference is generated.

A second signal processing method according to the present invention includes: receiving a signal obtained from an object as an input signal; generating a first order time lag signal from the input signal; generating a second order time lag signal from the first order time lag signal; calculating a difference between the first order time lag signal and the second order time lag signal; and detecting the generation of the difference so as to feature a portion of the object at a position where the difference is generated.

To achieve the above-described object, a first signal processing device according to the present invention includes: an input part for inputting a signal obtained from an object as an input signal; a time lag signal generating part for generating a time lag signal from the input signal; a difference generating part for calculating a difference between the input signal and the time lag signal; and a featuring part for featuring a portion of the object at a position where the difference is generated by detecting the generation of the difference.

A second signal processing device according to the present invention includes: an input part for inputting a signal obtained from an object as an input signal; a first order time lag signal generating part for generating a first order time lag signal from the input signal; a second order time lag signal generating part for generating a second order time lag signal from the first order time lag signal; a difference generating part for calculating a difference between the first order time lag signal and the second order time lag signal;

and a featuring part for featuring a portion of the object at a position where the difference is generated by detecting the generation of the difference.

A third signal processing device according to the present invention includes: a circuit module for inputting a signal obtained from an object as an input signal; a circuit module for generating a time lag signal from the input signal; a circuit module for calculating a difference between the input signal and the time lag signal; and a circuit module for featuring a portion of the object at a position where the difference is generated by detecting the generation of the difference.

A fourth signal processing device according to the present invention includes: a circuit module for inputting a signal obtained from an object as an input signal; a circuit module for generating a first order time lag signal from the input signal; a circuit module for generating a second order time lag signal from the first order time lag signal; a circuit module for calculating a difference between the first order time lag signal and the second order time lag signal; and a circuit module for featuring a portion of the object at a position where the difference is generated by detecting the generation of the difference.

BRIEF DESCRIPTION OF THE DRAWINGS

FIG. 7 is a schematic diagram showing the data processing operated in a digital filter.

DESCRIPTION OF THE PREFERRED EMBODIMENTS

The following will describe the present invention by referring to signal processing in a rain sensor as an example.

(Measurement Principle)

First, a basic principle of the optical system employed in the object sensor is described with reference to FIG. 1.

Figure 1:
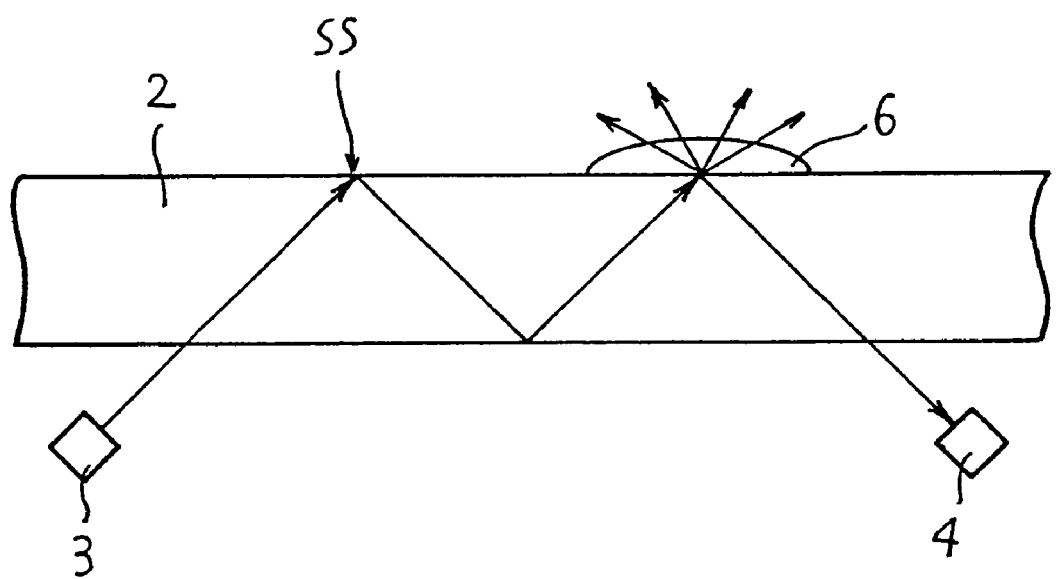
FIG. 1 is a schematic diagram showing a basic principle of an optical system employed in an object sensor of this invention.

For, example, as shown in FIG. 1, a light emitted from the photo emission element (3) such as LED is led to the transparent glass sheet (2) on which surface a water drop will be sensed. The led light causes a total reflection on the sensing surface, and for instance, the reflected light is received by the photo detector (4) such as a photo diode. The photo detector (4) is installed in the object sensor so that the output signal becomes maximum when no water drop exists on the sensing surface. Therefore, if there is a water drop present on the sensing surface, the output signal level of the photo detector will be decreased because of variation in the reflection condition at the sensing surface. The object sensor of this invention detects the decease of the output signal level and judges the dynamic water drop impacting the sensing surface.

Figure 2:
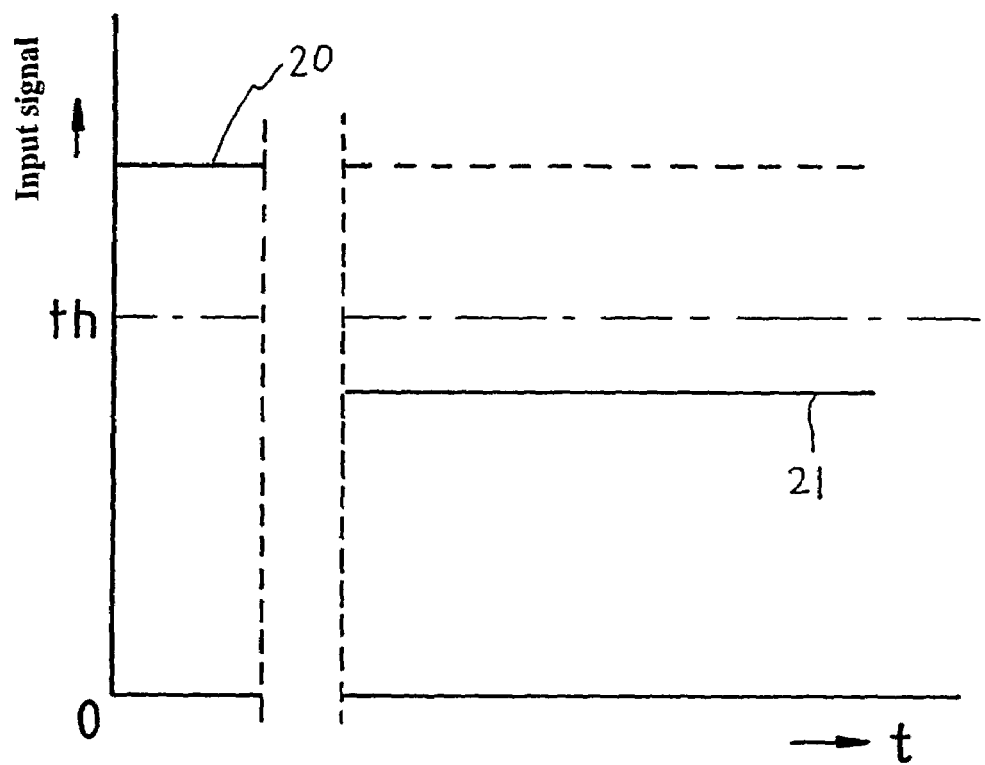
FIG. 2 is a schematic diagram showing the signal model of the photo detector and the decrease of the signal level in the case that a water drop is present on the sensing surface statically.

FIG. 2 shows the input signal model inputted from the photo detector in the case that a water drop exists on the sensing surface statically and in the case that no water drop exists on the sensing surface. The signal level (20) shows the case where no water drop exists on the sensing surface. On the other hand, the signal level (21) shows the case where a water drop exists on the sensing surface. The vertical axis indicates the value of the input signal, and the horizontal axis indicates the time base.

When a water drop exists on the sensing surface statically and the status of the water drop does not vary, there will be no varying in the signal level of the photo detector. Therefore, the time lag signal of this signal level is not generated. Of course, the differential value between the input signal and the time lag signal is not generated. In this case, when the signal level becomes lower than the appropriately preset threshold (th), the object sensor may judge the existence of a water drop.

FIG. 3(a) shows an example of the input signal model in the case that a water drop is impacting on the sensing surface dynamically. The output signal of the photo detector is inputted (shown as $D_{IN}$). The signal of the time lag element (F1) can be generated from this input signal ($D_{IN}$). Furthermore, the differential signal ($\Delta(F1-D_{IN})$) calculated by subtracting the above mentioned input signal ($D_{IN}$) from the above-mentioned time lag signal (F1) can be generated. FIG. 3(b) shows an example of the generated differential signal model. In the differential signal ($\Delta(F1-D_{IN})$), a positive difference is generated between t0 and t1, and a negative difference is generated between t1 and t3.

Figure 3:
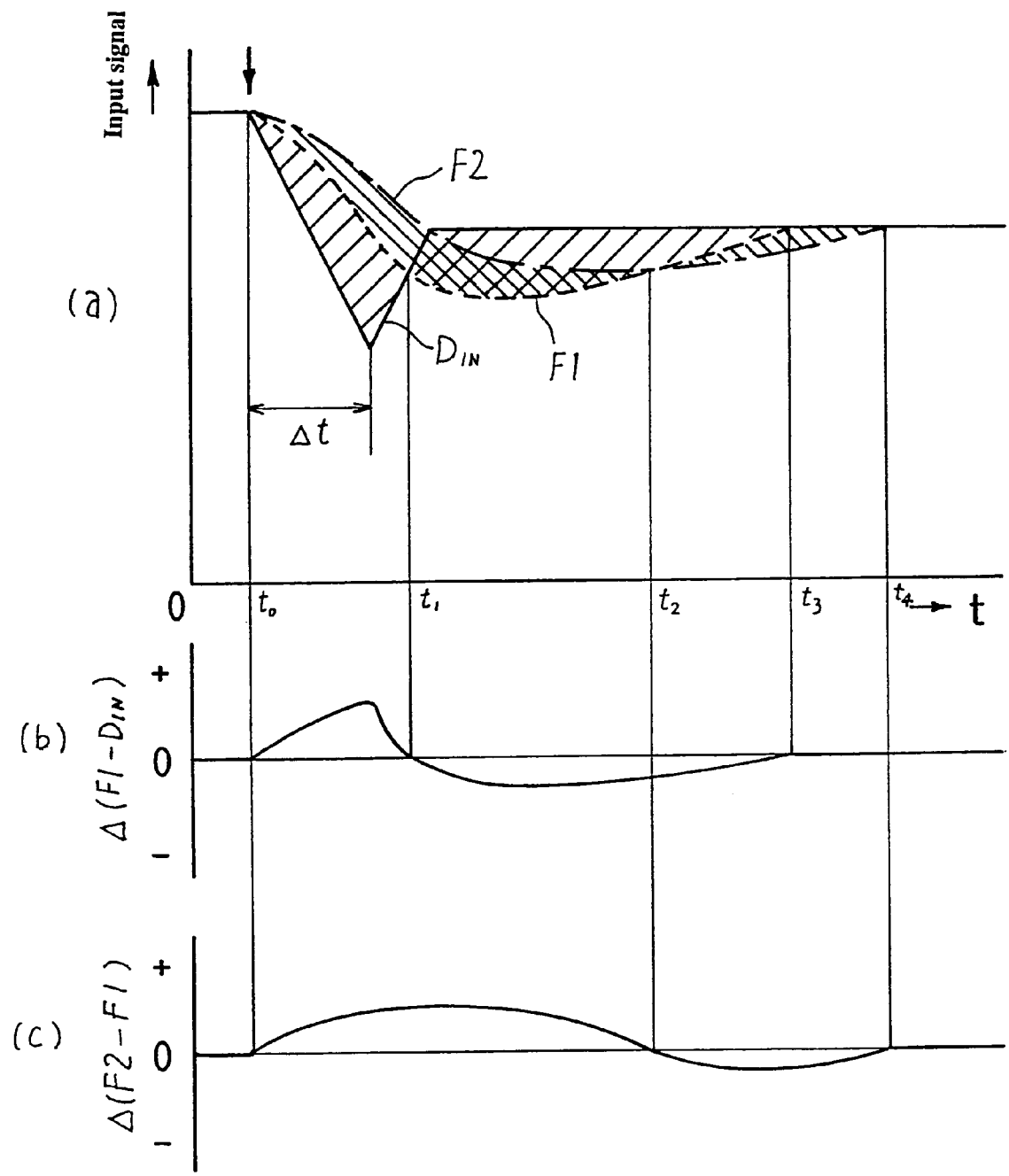
FIG. 3 is a schematic diagram showing a basic principle of the measurement method of this invention.

In FIG. 3(a), a water drop begins to impact the sensing surface at the time (t0) where the arrow indicates, and a period indicated by Δt corresponds to the situation that the water drop is collapsing. The subsequent signal part of a smooth level corresponds to a signal model showing the situation in which the water drop has collapsed and extended. When comparing the signal detected in case that a water drop exists on the sensing surface statically and the signal detected in case that a water drop impacting the sensing surface dynamically, it is understood that the differential signal shown as FIG. 3 has been generated in the latter case but not in the former case. In short, a water drop impacting on the sensing surface can be detected by detecting the generated differential signal. When the above mentioned differential signal is defined as a value ($\Delta(F1-D_{IN})$) calculated by subtracting the above mentioned input signal ($D_{IN}$) from the above-mentioned time lag signal (F1), if the above mentioned differential signal is positive, the object sensor can detect the fact that a water drop has impacted the sensing surface. If a dynamic water drop that impacts the sensing surface dynamically can be detected, the dynamic control of the windshield operation corresponding to the result of the sense of the dynamic water drop can become possible by counting the number of the water drops impacting the sensing surface. In both of the above mentioned cases, a water drop exists on the sensing surface. Therefore, the conventional rain sensor using a conventional threshold method (which compares the input signal value with the reference values) will sense a water drop as same in either case.

The problem of the conventional rain sensor is that if the size of a water drop that exists on the sensing surface is small, the decrease of the signal level inputted from the photo detector becomes small. Therefore, the conventional threshold method can not set such a small threshold value appropriately because such a small value is the same level as noise. That is, if the size of a water drop present on the sensing surface is small, the water drop cannot be sensed by the conventional threshold method. On the contrary, the present invention can sense a rain drop impacting the sensing surface dynamically, and a rain drop can be sensed adequately even though a rain drop to be sensed is small and the signal level is difficult to be distinguished from the noise level. In short, even though the water drop is small, the windshield wiper controller can drive the wiper arm adequately when the windshield is to be cleared. Therefore, the case where a malfunction may happen can be reduced by applying the present invention. Here, the "malfunction" of the windshield wiper using the rain sensor means the case where a necessary operation is not carried out at the necessary time or an unnecessary operation is operated at an unnecessary time.

As explained above, in the water drop sensing method in which the present invention is applied, a varying of the status of the sensing surface is detected as a differential variation of the signal level. On the other hand, in the conventional threshold value method, a varying of the status of the sensing surface is detected as an integrated variation.

Therefore, the water drop sensing method in which the present invention is applied can detect a fine variation of the status of the sensing surface.

In the above description, the object sensor senses a water drop by detecting the generation of the differential signal ($\Delta(F1-D_{IN})$) calculated by subtracting the input signal ($D_{IN}$) from the time lag signal (F1).

Furthermore, it is preferable that the object sensor generates a second order time lag signal (F2) from a first order time lag signal (F1), and generates the differential signal ($\Delta(F2-F1)$) calculated by subtracting the second order time lag signal (F2) from the first order time lag signal (F1), and senses a water drop by detecting the generated differential signal ($\Delta(F2-F1)$) (FIG. 3(c) is to be referenced).

The reason of the advantage of the above mentioned processing is as follows. The A/D converted input signal includes the quantization noise, and the pattern processing using the differential signal is suitable for detecting the fine difference but is weak as to the noise in general. In the differential signal ($\Delta(F2-F1)$), a positive difference is generated between t0 and t2, and a negative difference is generated between t2 and t4.

The following will describe the present invention in more detail.

Embodiment 1

First, the optical system employed in a rain sensor as an application example of the present invention is described below.

Figure 4:
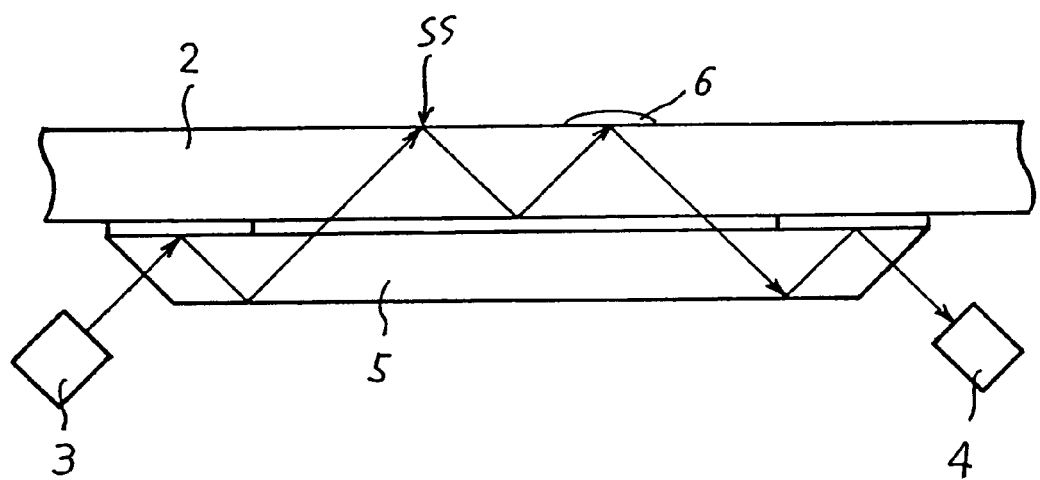
FIG. 4 is a schematic diagram showing a basic configuration of the optical system that can be applied to the object sensor of this invention.
Figure 5:
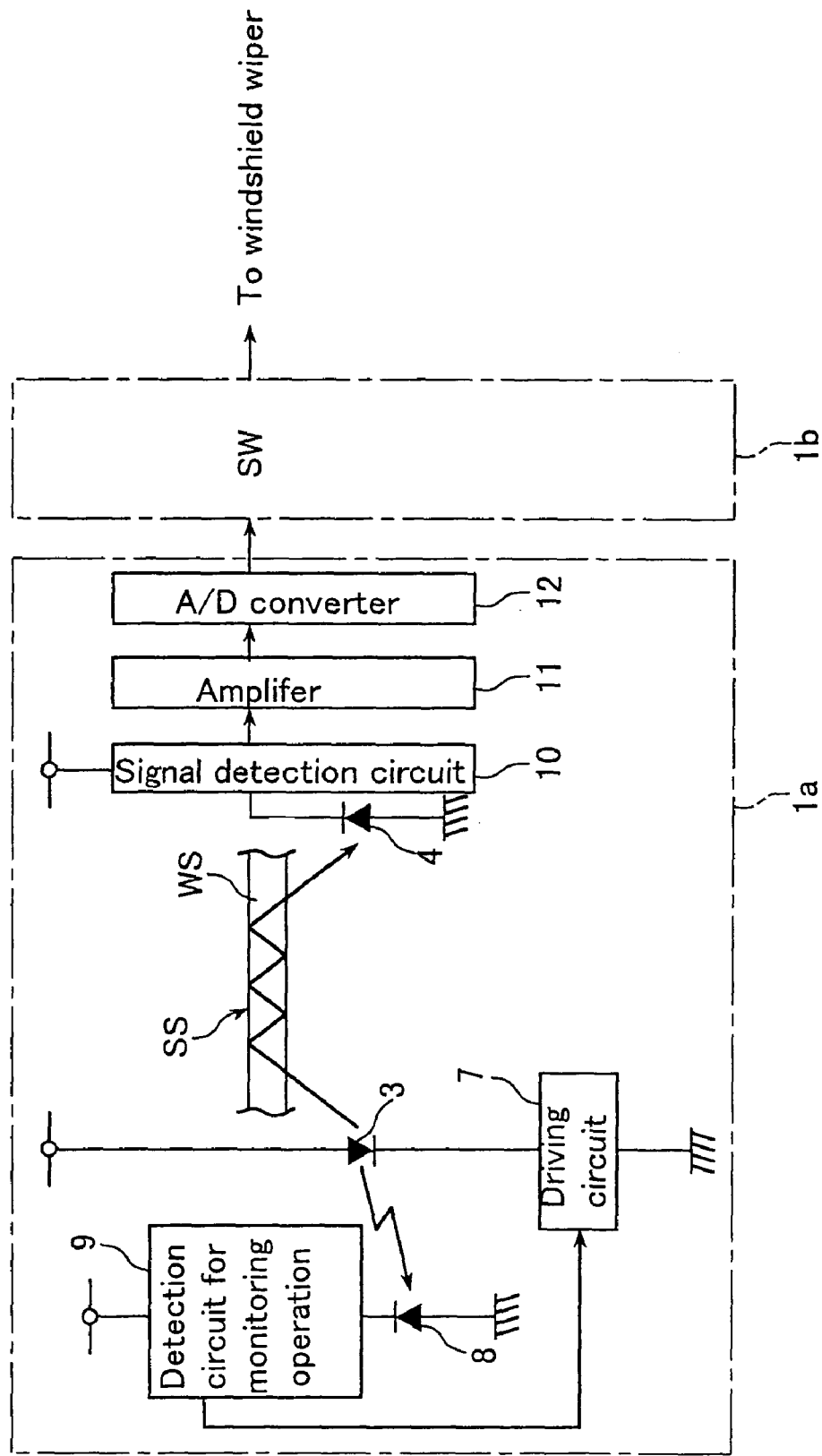
FIG. 5 is a block diagram showing the configuration of the hardware of the object sensor of Embodiment 1 of this invention.
Figure 6:
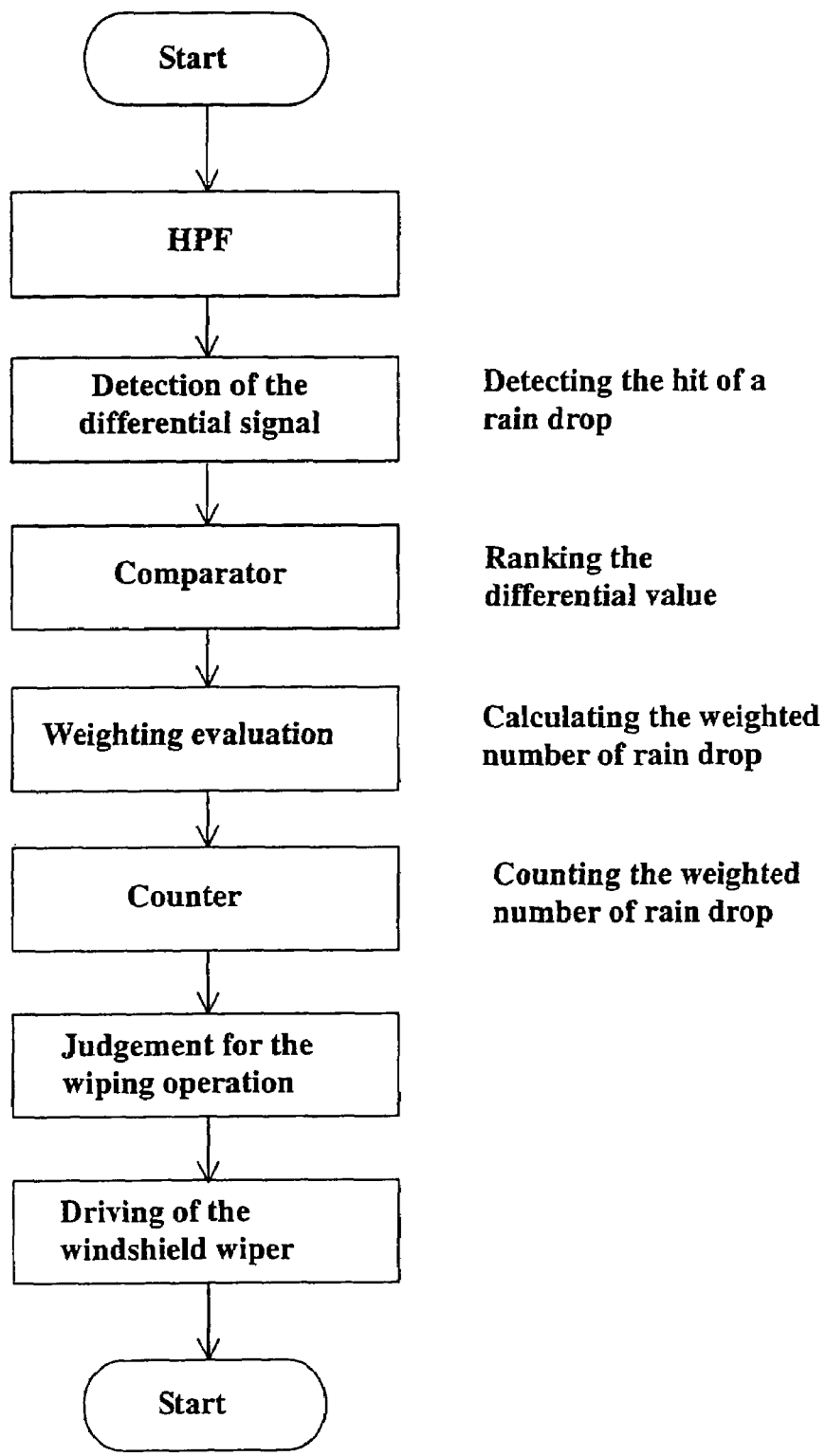
FIG. 6 is a flowchart showing the object sensing operations of this object sensor of this invention and windshield wiper driving operations of this invention.

FIG. 4 is a diagram showing a basic configuration of the optical system applied to the object sensor of this Embodiment 1. FIG. 5 is a block diagram showing the configuration of the hardware of the object sensor of Embodiment 1 of this invention. FIG. 6 is a flowchart showing the object sensing operations of this object sensor of this Embodiment 1.

For, example, as shown in FIG. 4, a light emitted from the photo emission element (3) such as LED is led to the transparent glass sheet (2) on whose surface a water drop will be sensed. The led light causes a total reflection on the sensing surface (SS), and for instance, the reflected light is received by the photo detector (4) such as a photo diode via prism glass (5). In the object sensor shown in this Figure, the photo detector (4) is installed so that the output signal becomes maximum when there is no water drop present on the sensing surface (SS). Therefore, if there is a water drop (6) on the sensing surface (SS), the output signal level of the photo detector will be decreased because of the variation of the reflection condition at the sensing surface. The photo emission element may be driven by a carrier pulse whose frequency (carrier frequency) is 500 Hz or more. It is preferable that the actual amount of the light emitted from the photo emission element (3) is monitored by a photo detector (8) for monitoring the operation and a circuit module (9) for monitoring the operation of the photo emission element because of the temperature characteristics of the photo emission element (3). It is preferable to drive the photo emission element (3) by the driving circuit (7) while feeding back the monitoring result (FIG. 5).

As shown in FIG. 5, when the light is received in the photo detector (4) in the hardware module (1a), the output signal is generated. At this moment, the detected signal includes carrier pulses used for driving the photo emission element, so that a significant real signal is taken out by the signal detector (10). It is preferable that the signal outputted from the photo detector (4) is amplified by the amplifier (11) because it is normally difficult to obtain a large volume signal outputted by the photo detector available in commercial use. Continuously, the amplified signal is inputted to the A/D converter (12), and converted into digital data. At this time, the dynamic range of the A/D converter (12) can be set properly according to the output signal of the optical system mentioned above.

It should be noted that the object sensor comprises the hardware module (1a) and the software module (1b).

Next, the water drop sensing operation logic employed in the object sensor of the present invention is described (FIG. 6 is to be referenced). It is preferable that the output of the A/D converter (12) is previously inputted into a noise canceling filter in order to cancel the spike noises generated by an irregular light coming from inside or outside of the car. This noise canceling processing also can be performed with software.

[LPF1]: Removal of Quantization Noise

First of all, the output of the noise canceling filter is inputted to the first digital filter such as low pass filter (LPF1). This LPF1 is used for eliminating the quantization noise generated in the digital conversion at the A/D converter (12) and canceling the noise generated in the other circuit modules used in the former stage. The output (F1) from the LPF1 can be understood as the first order time lag signal from the input signal ($D_{IN}$). The noise canceling processing in this LPF1 is performed as follows. The sum of the predetermined number of sampling signals inputted sequentially is calculated, and is divided by the number of the sampled signals so as to be leveled out. On this LPF1, the above mentioned predetermined number of samples is determined so as to cancel the spike noises to some extent.

The above mentioned predetermined number of samples is determined as follows. Measure the maximum noise level that can be assumed in this circuit and set the digital value corresponding to the maximum noise level. The above mentioned predetermined number of samples is determined so as to eliminate the maximum level noise, in short, the number is determined as the value calculated by leveling out the digital value with the number of samples so as to become "0". Normal level noise can be eliminated by leveling out the input value sequentially. It is preferable that the data processing by this invention does not perform the floating point processing and omits decimals for high-speed processing.

By referring to FIG. 7, the level processing is described in detail. It is assumed that there is input data D(n) and data cells used in leveling processing. For example, when the number of samples to be leveled out is assumed to be "8", 8 data cells are used and data D1 to D8 fetched from D(n) are inputted to data cells sequentially. The sum of these 8 data is divided by the sample number "8" and the leveled value (F(1)) is outputted. Next, the data D9 is inputted to a data cell and the data D1 is shifted out in turn. In the same way as shown above, the sum of current 8 data is divided by the sample number "8" and the leveled value (F(2)) is outputted. The leveling processing is performed in the same way.

[LPF2]: Generation of Time Lag Signal

The quantization noise-cancelled signal (F1) is inputted to the second digital filter such as low pass filter (LPF2). This LPF2 levels out the predetermined number of signals sampled sequentially by summing the sampled signals and dividing the sum by the number of the sampled signals in the same manner as the LPF1 does. The time lag signal (F2) can be generated from the signal (F1) by the leveling process as mentioned above. The output signal (F2) from the LPF2 can be understood as the second order time lag signal from the input signal ($D_{IN}$). Two stage filtering mentioned above can be understood as a low pass filter that cuts the high frequency component. This process can be achieved in the analog circuit as described later.

[HPF]: Generation of Differential Signal

The output signal of the above mentioned LPF1 and the output signal of the above mentioned LPF2 are inputted to the third digital filter such as high pass filter (HPF3). The differential signal is generated by calculating the difference between the above-mentioned signal F1 and the signal F2. For instance, signal F1 is subtracted from the signal F2. The filtering processing for generating the differential value can be understood as a high pass filter that extracts the high frequency component from the differential signal between the above-mentioned signal F1 and the signal F2.

[Detection of Differential Signal]: Detection of Dynamic Impact of an Object

A dynamic impact of an object such as a water drop can be sensed by detecting the differential signal generation. For instance, when the differential signal is assumed to be a value calculated by subtracting the signal F1 from the signal F2, and if the above mentioned difference value is positive, it can be assumed that the impact of the object such as a water drop on the sensing surface has happened. Oppositely, when the differential signal is assumed to be a value calculated by subtracting the signal F2 from the signal F1, and if the above mentioned difference value is negative, it can be assumed that the impact of the object such as a water drop on the sensing surface has happened.

The differential signal detection of the object sensor in an example of a configuration using the following elements is described. The optical system shown in FIG. 4 was used, and the photo detector and photo emission element as shown were used.

Photo emission element: LED; Made by Kyoto Semiconductor, KED352RHA

Photo detector: PD; Made by Kyoto Semiconductor, KPD4503K

In addition, the current/voltage conversion is carried out on the output of the photo detector by the following IC and it is amplified. The A/D conversion is carried out by the A/D converter built in the CPU. The A/D converted signal is inputted to the CPU and the software processing mentioned above is carried out on the signal.

The current/voltage converter and amplifier: Made by NEC; µ PC844

CPU: Made by Hitachi; H8S/2134 (A/D converter built in)

The canceling of the quantization noise (the first order time lag signal (LPF1)) is processed by leveling out 8 data (n=8), and the generation of the time lag signal (the second order time lag signal (LPF2)) is conducted by leveling out 4 data (n=4). The reason that the number of data in LPF2 is less than that of LPF1 is that the noise already has been cancelled by LPF1.

Figure 8:
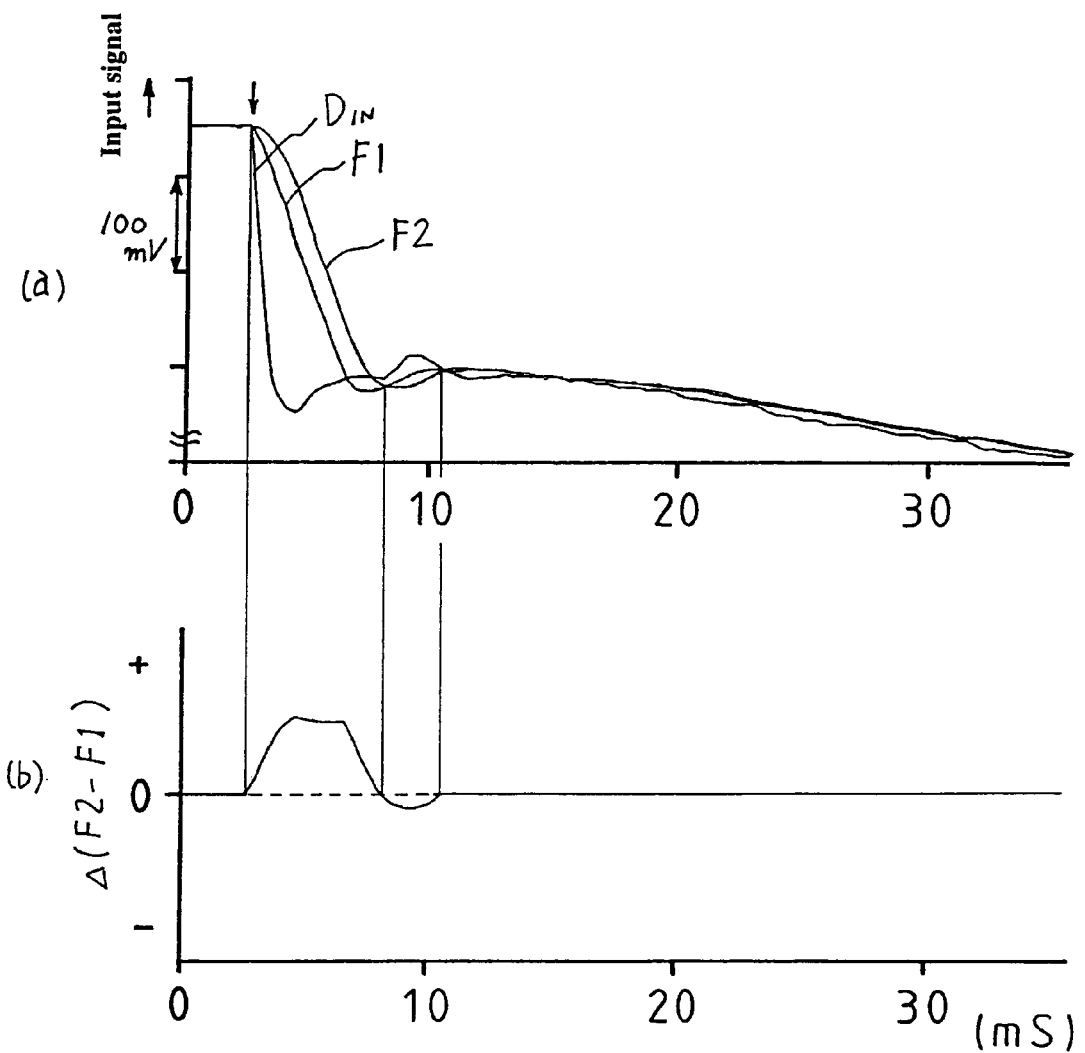
FIG. 8 is a schematic diagram showing the signal level of the photo detector and the processed signal level when a rain drop impacts the sensing surface.

FIG. 8 is a diagram showing an actual example of the signal level of the photo detector and the processed signal level where a rain drop impacts the sensing surface.

The graph FIG. 8(a) shows the actual input signal ($D_{IN}$), the noise-cancelled first order time lag signal (F1) and the second order time lag signal (F2). The graph FIG. 8(b) shows the differential signal calculated by subtracting signal F1 from signal F2. The horizontal axis is a time base. The rain drop began to impact the sensing surface at the timing of the arrow (↓) shown in the figure. It is clearly understood from FIG. 8 that a positive differential signal ($\Delta$(F2−F1)) had been generated corresponding to the impact having a magnitude of the rain drop.

In addition, the following can be confirmed by the result shown in FIG. 8. That is, when generating the time lag signal (F2) from the noise-cancelled signal (F1), the time lag signal will become large when the signal F1 varies rapidly, and on the contrary, the time lag signal will become small when the signal F1 does not vary so much. In addition, when generating the differential signal between signal F2 and signal F1 ($\Delta$(F2−F1(F1))), the differential signal will be enhanced and become large when the signal F1 varies rapidly, and on the contrary, the differential signal will not be generated when the signal F1 does not vary so much. Moreover, for instance, when the output of the photo emission element shifts slowly, the output of the photo detector also shifts. In this case, the accurate detection by the conventional rain drop sensing method using the fixed threshold value is difficult as described in the prior art. Therefore, the complex judgment logic should be required in the conventional method. On the contrary, with the object sensing method of the present invention using the detection of the differential signal of the first order time lag signal (F1) and the second order time lag signal (F2), the amount of the shift can be cancelled by taking the differential value, so that an appropriate rain drop sensing corresponding to the rain drop impact becomes possible.

Figure 9:
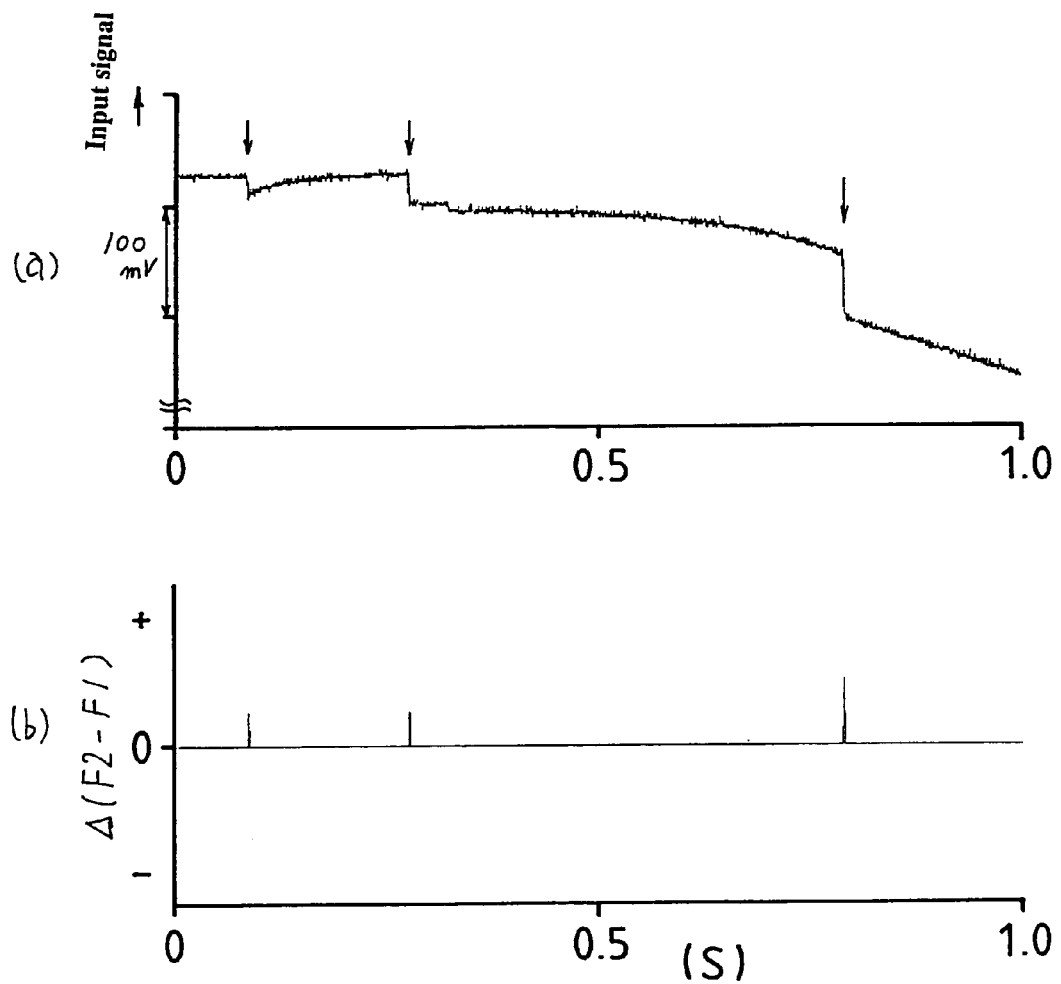
FIG. 9 is a schematic diagram showing the signal level of the photo detector and processed signal level when a fine rain drop impacts the sensing surface.
Figure 10:
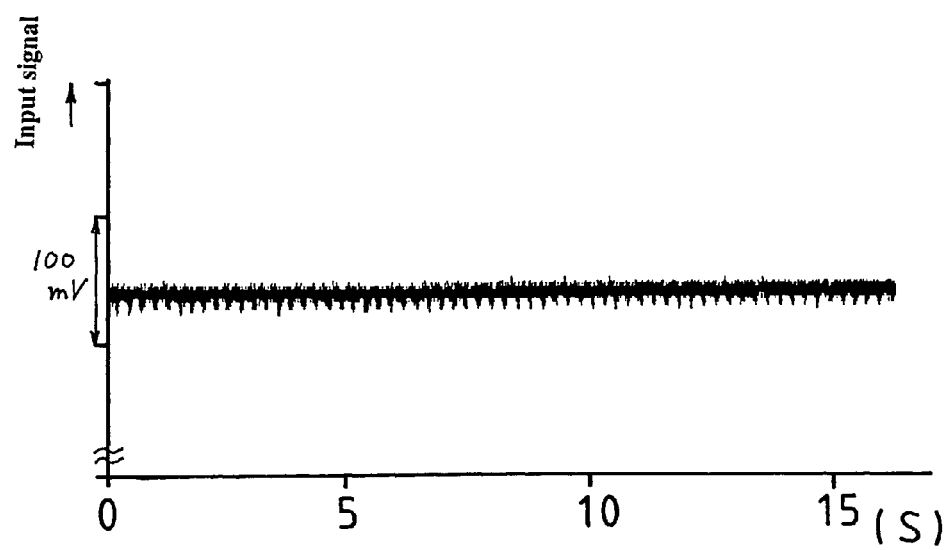
FIG. 10 is a schematic diagram showing the noise level included in the signal level of the photo detector used in this Embodiment 1.

Next, FIG. 9 shows the actual example of the signal when a small rain drop impacts the sensing surface. In FIG. 9, a rain drop impacts the sensing surface at the timing of the arrow (↓) shown in figure. The time base of the horizontal axis is different from that of FIG. 8. In addition, the noise level of this practical object sensor was about 25 mV as shown in FIG. 10. The amount of variation of the signal when a small rain drop impacted was about 23 mV or about 30 mV, and this level was not so much different from the noise level. However, it was able to be detected as a positive differential signal generated corresponding to the impact of the small rain drop. In other words, with the present invention, even a small rain drop impact having a magnitude of a noise level can be detected accurately.

[Counting Processing & Judging Processing]

The number of rain drops impacting the sensing surface sensed by the above mentioned method is counted by the counter, and the driving operation of the windshield wiper may be controlled according to the accumulation of the counted number (Refer to FIG. 6). The counted number can be reset by receiving every wiping signal indicating the instruction for wiping off the windshield.

Embodiment 2

Following is the description of the object sensor of Embodiment 2 of this invention. In Embodiment 2, another example of the hardware configuration of the object sensor of this invention that is different from that of FIG. 5 shown in Embodiment 1 is described. In the configuration shown in Embodiment 1, the analog signal inputted from the signal detection circuit 10 is converted into the digital signal by A/D conversion, and the noise canceling processing and/or the time lag signal generating processing were/was executed by the software processing means. In the configuration shown in this Embodiment 2, the analog signal inputted from the signal detection circuit 10 is used as an analog signal as it is, and the noise canceling processing and/or the time lag signal generating processing were/was executed by the analog circuit module generating the time lag signal. The optical system used in the object sensor of this Embodiment 2 can be the same optical system shown in FIG. 4 described in Embodiment 1, so that the description of the optical system used in this Embodiment 2 will be omitted here.

Figure 11:
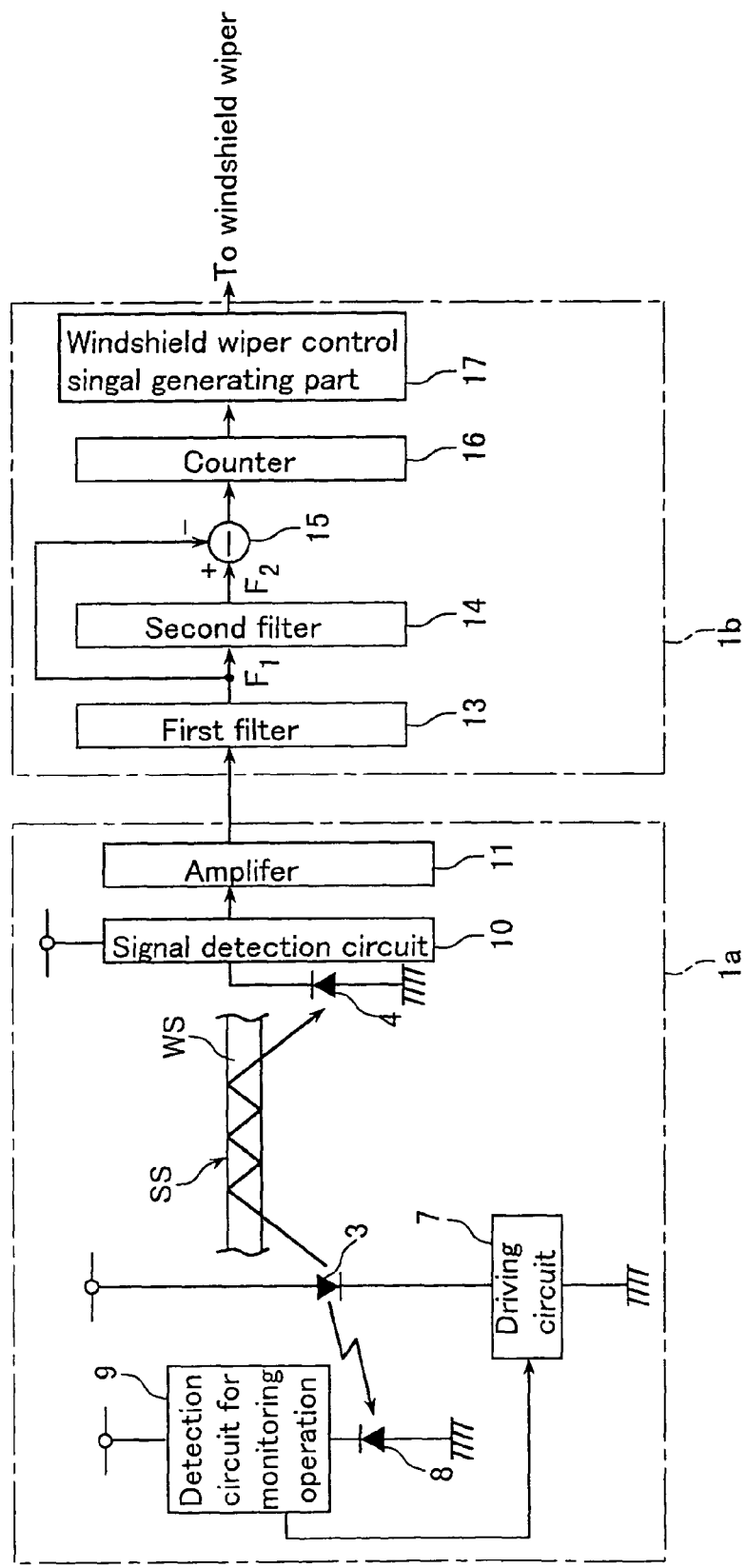
FIG. 11 is a block diagram showing the configuration of the hardware of the object sensor of Embodiment 2 of this invention.

FIG. 11 is a block diagram showing the hardware of the object sensor of the Embodiment 2. In FIG. 11, the hardware circuit modules (1a) of a former section of the object sensor, the windshield (WS), the photo emission element (3), the photo detector (4), the driving circuit for photo emission element (7), the photo detector (9) for monitoring the operation, the signal detector (10), and the amplifier (11) can be similar respectively to the ones having the same element number of the circuit module of the former section in FIG. 5 shown in Embodiment 1. In FIG. 11, the hardware circuit modules (1b) of a latter section of the object sensor comprises the first filter (13), the second filter (14), the differential circuit (15), the counter circuit (16), and the windshield wiper control signal generation part (17).

The first filter (13) and the second filter (14) are the circuit modules for inputting the analog signal and outputting the processed analog signal after filtering, and these work as analog circuit modules for generating the time lag signal from the input signal. In FIG. 11, as an example, LC filters can be used as the first filter and the second filter, however, it is not limited to this example. Other examples such as RC filters can be another example as long as these can generate the time lag signal from the input signal. The relationship of the input signal and the output signal of the first filter (13) and the second filter (14) is the same as FIG. 3 and FIG. 8 shown in Embodiment 1, the output signal of the first filter (13) becomes F1 when the input signal is $D_{IN}$, and the output signal of the second filter (14) becomes F2 when the input signal is F1.

The differential circuit (15) has 2 input terminals, and it outputs the differential signal of the 2 input signals. When the configuration of the differential circuit is shown as FIG. 11, the output signal F1 of the first filter (13) and the output signal F2 of the second filter (14) are received as input signals and the differential signal $\Delta(F2-F1)$ is outputted. The output signal $\Delta(F2-F1)$ of the differential circuit (15) becomes the same as the one shown in FIG. 3 and FIG. 8 described in Embodiment 1.

The counter (16) is a circuit that counts a positive differential signal appearing in the output signal $\Delta(F2-F1)$ of the subtractor (15). For instance, in the case of using the threshold method in the counting processing, the output signal $\Delta(F2-F1)$ of the subtractor (15) is inputted to the built-in comparator having a positive predetermined reference value as a threshold, and when the input signal value exceeds the threshold, the counted value is increased by one. The count value is outputted to the windshield wiper control signal generation part (17). The comparison processing with the threshold is included in the processing of the counter (16), but the counting processing by the threshold method can be performed correctly because the shift of the background and the noise are cancelled from the input signal.

The windshield wiper control signal generation part (17) is a control unit that receives the signal from the counter (16), generates the wiping off operation control signal of the windshield wiper according to the detected signal number or the detected signal frequency in the predetermined period and provides the generated operation control signal to the windshield wiper. The tuning of the control signal of the wiping off operation is possible. For instance, the control signal can be tuned as the signal for starting the wiper for the wiping off operation immediately according to the signal from the counter (16). In other cases, when the control signal is received the first time, the wiper does not perform wiping operation and when the control signal is received at the second time, the wiper performs wiping operation. Furthermore, the signal can be tuned as a signal for switching the wiping frequency according to the signal detection frequency in the predetermined period.

Figure 12:
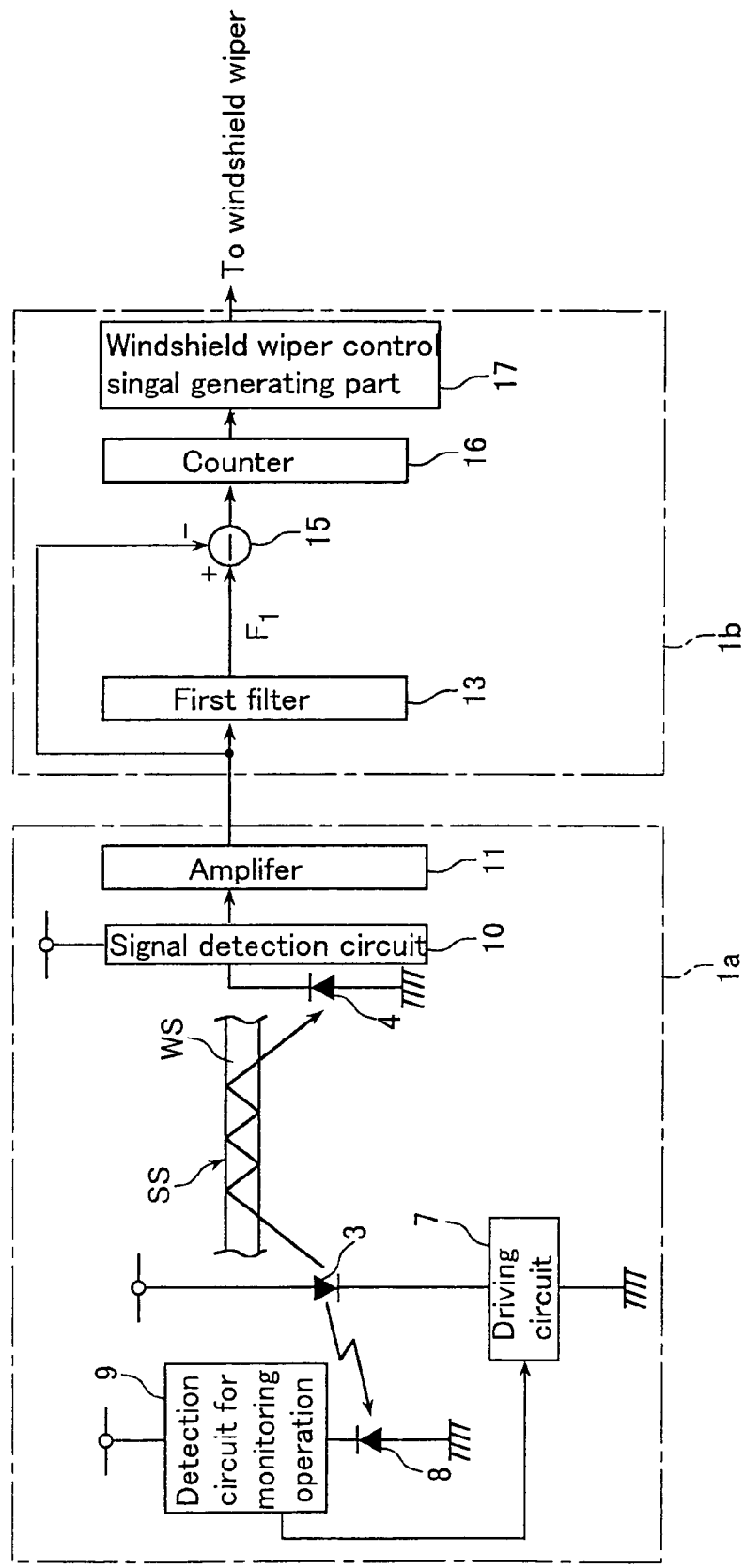
FIG. 12 is another block diagram showing the configuration of the hardware of the object sensor of Embodiment 2 of this invention.

In the above mentioned configuration, the first filter (13) and the second filter (14) are installed and the signals from these 2 filters are inputted to the subtractor (15). However, another configuration that uses only the first filter (13) and omits the second filter (14) as shown in FIG. 12 can be possible. In this case, the 2 input signals of the subtractor

(15) will be the input signal $D_{IN}$ and the output signal F1 of the first filter (13). In this case, the output signal of the subtractor (15) becomes $\Delta(F1-D_{IN})$ as shown in FIG. 3(b). The counter (16) detects and counts a positive differential signal $\Delta(F1-D_{IN})$ as shown in FIG. 3(b).

APPLICATION EXAMPLE 1

In a method in which the present invention is applied, it is also possible to judge the status on the sensing surface according to the value of the differential signal.

For instance, because the size of the rain drop is not constant, the evaluation of sensing of a rain drop is weighted according to the size of the rain drop, the status of the windshield can be evaluated by the weighted value, which can be regarded as the number of the rain drop or frequency of the rain drop. For instance, when a large-size rain drop impacts the sensing surface, a big differential signal will be generated by a rapid and big variation in the signal F1. It is confirmed in the practical experiment that the generated differential value corresponds to the size of the rain drop. Then, the weighting to the impact of an individual rain drop can be performed by setting plural different thresholds for the generated differential signal.

Figure 13:
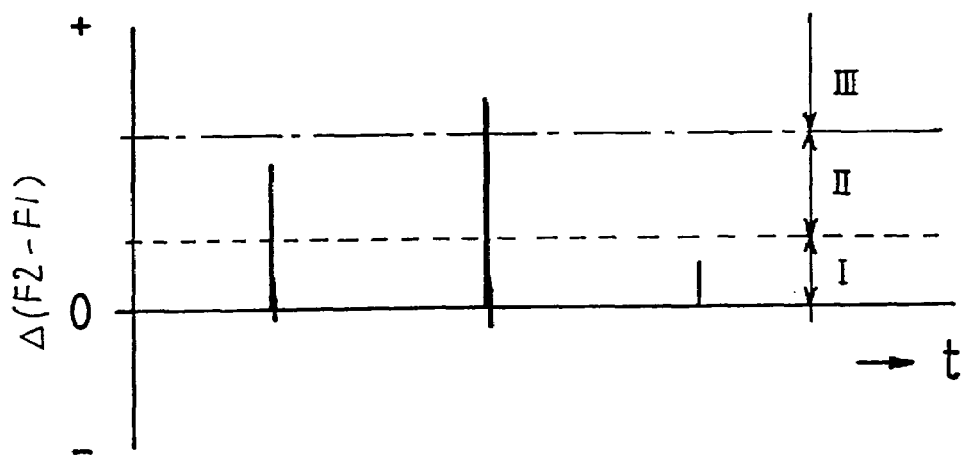
FIG. 13 is a schematic diagram showing a basic principle of the weighting of the difference by plural thresholds of Application Example 1 of this invention.
Figure 14:
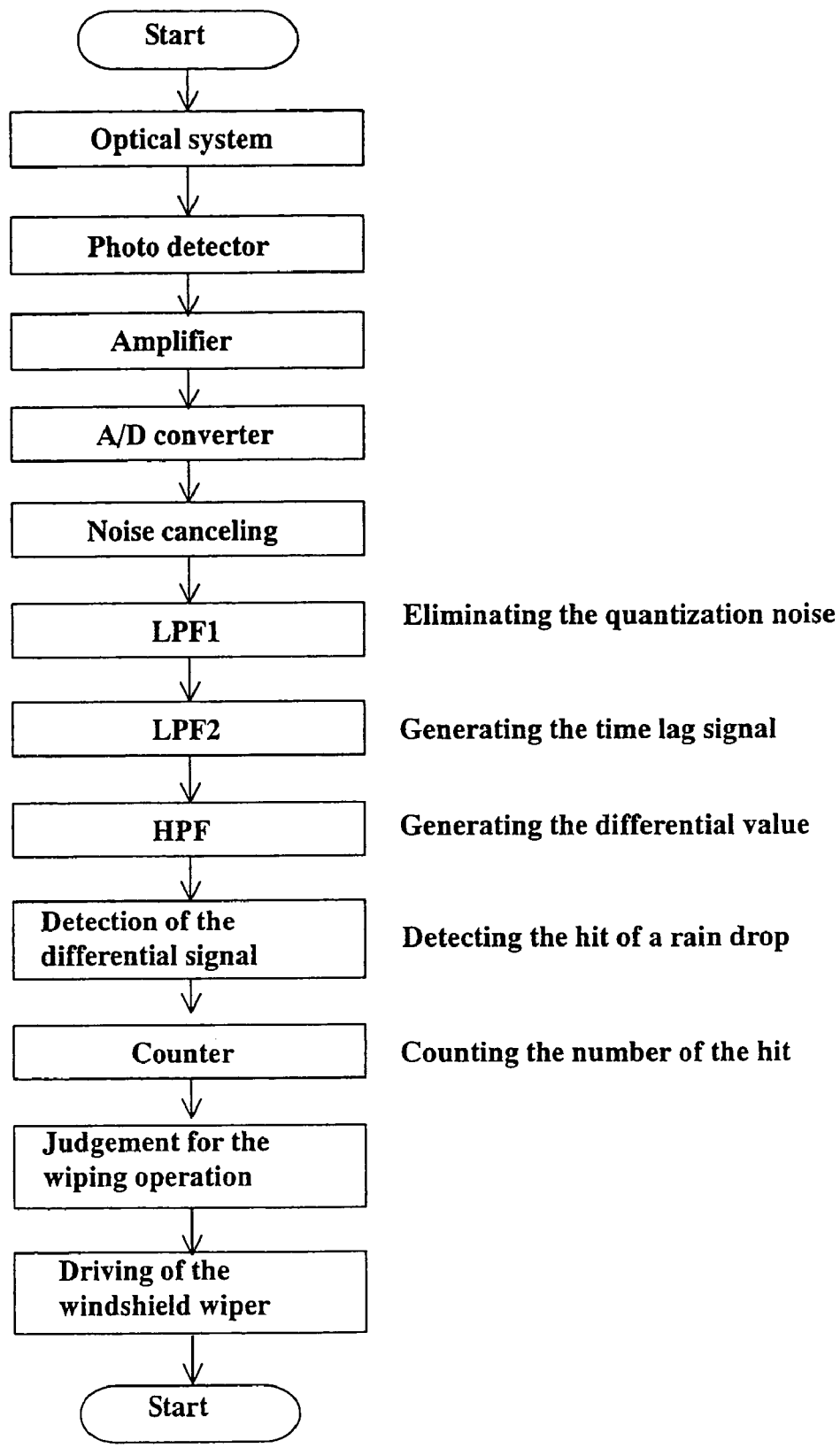
FIG. 14 is a flowchart showing the object sensing operations using weighting processing of Application Example 1.

FIG. 13 shows one example. As for the generated differential signal, the peak value is different according to the size of the impacting rain drop. Two thresholds are set here, and the rain drop is divided into three ranks (I,II,III). For weighting using this rank classification, the comparator having these two thresholds is used. The differential signal is inputted to the comparator. For instance, the weighting coefficient of rank I is assumed to be one, the weighting coefficient of the rank II is assumed to be two, and the weighting coefficient of the rank III is assumed to be three. The object sensor calculates the weighted value by multiplying the number of the differential signal by the above-mentioned weighting coefficient according to its rank, and accumulates those products while matching the timing of the differential signal detection. The example weighted value of total for FIG. 13 becomes 2+3+1=6. The weighting coefficient of each rank can be determined experimentally. The object sensor counts the weighted value obtained by the above mentioned calculation by using the counter, and the driving of the wiper can be controlled according to the accumulated number. FIG. 14 shows the flow chart of this processing.

Though the weighting evaluation mentioned shown above is processed by the comparison with the threshold, because the shift and the noise of the background are cancelled as for the input differential signal, the judgment by the threshold method can be performed correctly.

APPLICATION EXAMPLE 2

Figure 15:
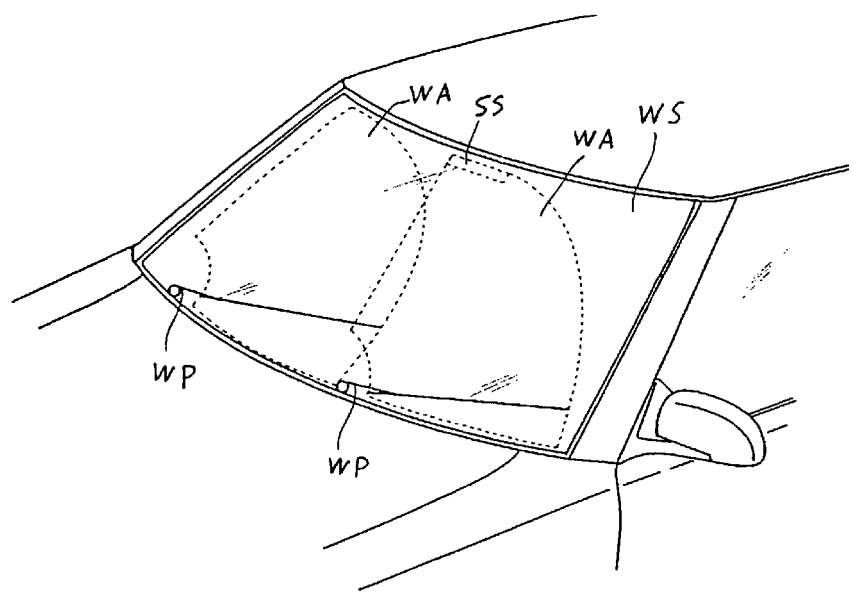
FIG. 15 is a schematic diagram showing the appearance where the object sensor of this invention is installed in a car.

FIG. 15 is a diagram showing the appearance where the rain sensor of this invention is installed in a windshield (WS) of a car.

The object sensor has been installed in the back of a rear view mirror (not shown in the figure) so as not to disturb the driver's view. In addition, the sensing surface (SS) of the object sensor is arranged within the range of wiping area (WA) of the wiper.

The impact of the rain drop on the sensing surface (SS) of the object sensor is detected by the object sensor. Then, for instance, the control signal from the wiper control signal generation part (17) shown in Embodiment 2 is supplied to the windshield wiper (WP), and the windshield wiper (WP) performs the wiping operation according to the control signal.

The above description describes a rain sensor as an example, but the present invention is not limited to a rain sensor, but may be applied to examples described below.

APPLICATION EXAMPLE 3

Figure 16A:
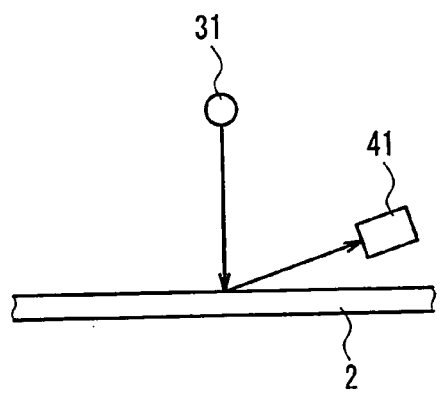
FIGS. 16A and 16B are schematic views illustrating a device for sensing defects in a glass plate.
Figure 16B:
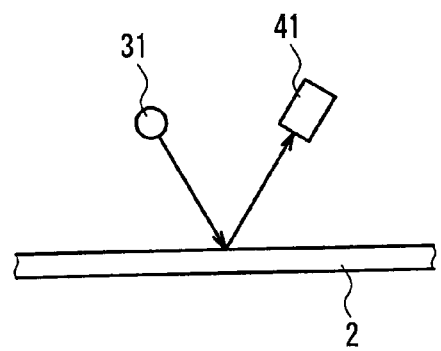

FIGS. 16A and 16B are schematic views of a device for sensing a defect of a glass plate, for instance. The sensor includes a line illuminating element 31 and a line sensor 41, and scans a surface of a ribbon glass plate 2 using the line sensor 41. In FIG. 16A, the line sensor 41 is arranged so as to receive diffused light from a defect present on the glass plate 2, for instance.

Figure 17:
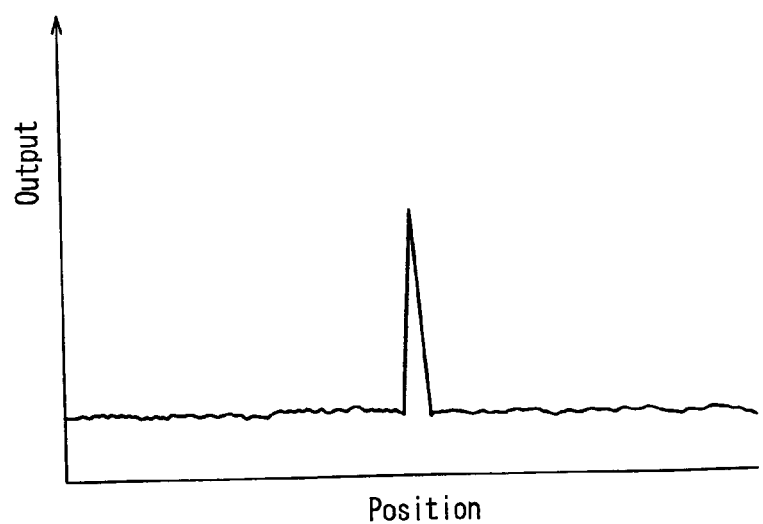
FIG. 17 is a schematic diagram of a scanning signal pattern of a dark-field-type defect sensor.

Since the sensor of FIG. 16A performs the sensing of the dark-field type, a normal portion is observed as a "dark" portion, while a defect portion is observed as a "light" portion. When the sensor scans the defect portion, a pulse-like "positive" peak appears at a position corresponding to the defect in a signal obtained from the line sensor, as shown in FIG. 17.

The present invention is not exclusively applicable to the dark-field-type defect sensor, but it also is applicable to a light-field-type defect sensor (see FIG. 16B). In the latter case, a normal portion is observed as a "light" portion, while a defect portion is observed as a "dark" portion. When the sensor scans the defect portion, a pulse-like "negative" peak appears at a position corresponding to the defect in the signal obtained from the line sensor.

The present invention is applicable, using the signal from the line sensor as an input signal. In other words, as is with the case of the above-described signal processing by the rain sensor, a difference is obtained by calculating a difference between an input signal and a time lag signal, and the generation of the difference is detected, whereby the defect portion can be sensed. It should be noted that the detection may be executed by obtaining a difference between a first order time lag signal and a second order time lag signal.

Even if fine noises are contained in an input signal, the noises can be cancelled by applying the signal processing method of the present invention. For instance, a difference between a first order time lag signal and a second order time lag signal may be obtained, or alternatively, a difference between the second order time lag signal and a third order time lag signal may be obtained. By so doing, the signal processing can be performed without being influenced by noises.

Further, for instance, even if the level of the input signal varies with temperature characteristics of a photo emission element and a photo detector, the application of the signal processing method of the present invention makes it possible to cancel the level variation. By so doing, the signal processing can be performed without being influenced by level variation of the input signal.

APPLICATION EXAMPLE 4

Further, the present invention also is applicable to image processing.

Figure 18:
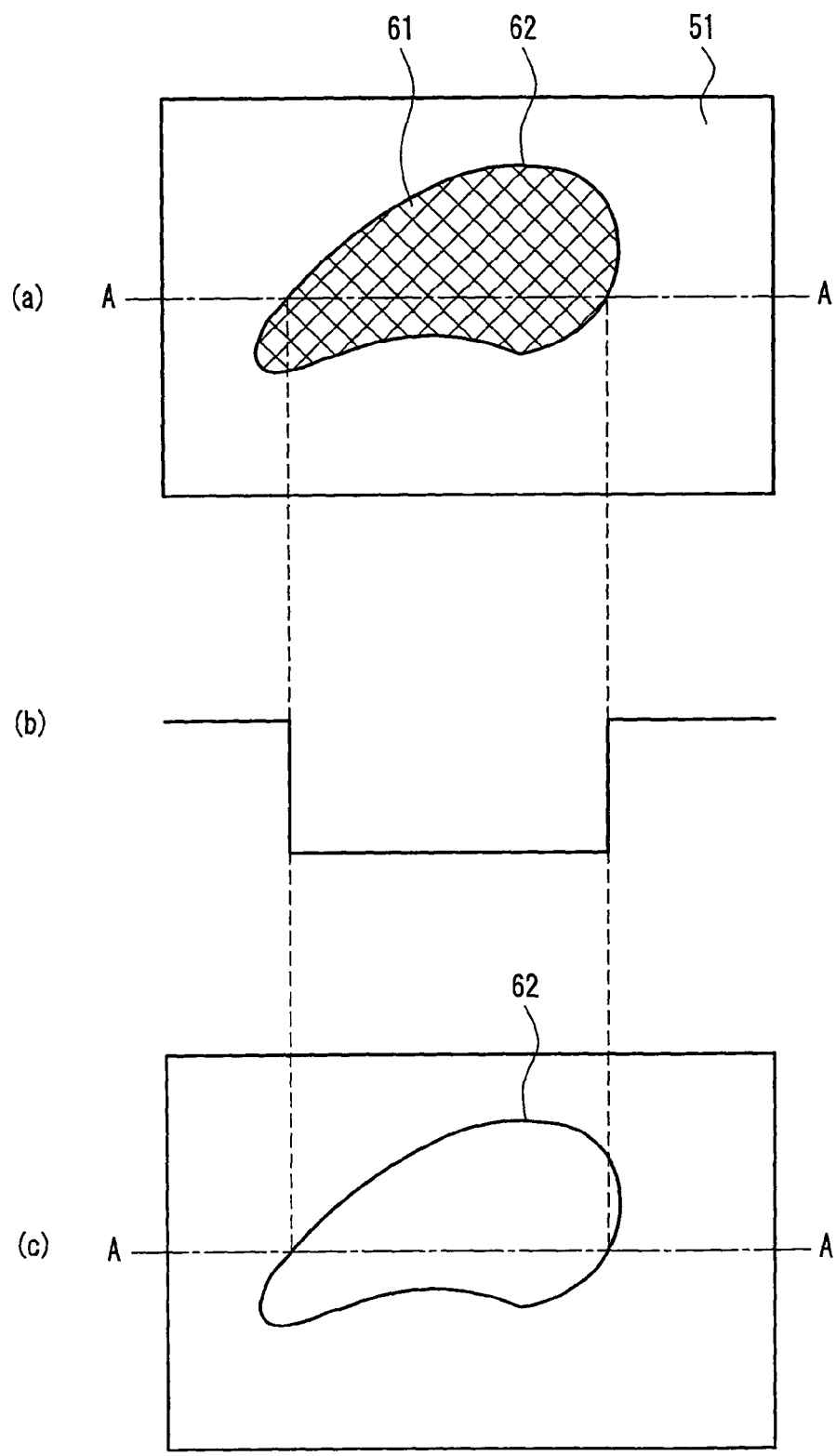
FIGS. 18A to 18C are a schematic view of an image obtained by imaging an object, a schematic diagram of a scanning signal pattern, and an extracted outline of the same, respectively.

For instance, it is possible to image an object with a television camera, and to use a scanning signal thereof as an input signal. FIG. 18A is a schematic view of an image 51 obtained by imaging an object 61, and FIG. 18B is a schematic diagram of a scanning signal pattern obtained when the object is scanned along a line A—A in FIG. 18A.

FIGS. 18A to 18C indicate a case where the object 61 has a lightness lower than the surroundings. The present invention is applied, with the scanning signal obtained in each scanning being supplied constantly, and positions at which differences are generated are featured as an outline of the object and are subjected to image processing according to the scanning. By so doing, only an outline of the object can be extracted (see FIG. 18C).

Application Example 5

The present invention also is applicable to the autofocusing technique, by further modifying the above-described outline extracting technique.

For instance, an object is imaged appropriately by moving a focus of a camera. The outline extraction is performed with respect to respective images thus imaged, and differences generated are stored. A focus position at which the difference is maximized is the focus position at which the outline of the object is made clearest, whereby it is determined that the object comes into focus when the focus is at the foregoing position.

As described above, the following effects can be achieved with the signal processing method and device of the present invention.

According to the present invention, by sensing a difference generated between an input signal and a time lag signal, a position in the object at which the difference is generated can be featured. It should be noted that the "featuring" is not limited to specific examples described as the foregoing embodiments and application examples. For instance, the qualitative detection of a state at a position in the object where a difference is generated falls in the concept of the "featuring". Further, for instance, the quantitative detection of a state at a position in the object where a difference is generated, and the extraction of a feature quantity from the difference quantity and labeling the position according to the extraction result, also fall in the concept of "featuring". Still further, the extraction of a feature or an attribute of the object at a position where a difference is generated also is regarded as an embodiment of the "featuring".

Thus, the signal processing method of the present invention only requires the detection of generation of a differential signal, which can be implemented by a simple judgment logic.

Furthermore, the signal processing method of the present invention is capable of canceling any level variation of an input signal, if any is generated therein, with temperature characteristics of a photo emission element and a photo detector.

Still further, the present invention is applicable to the image processing technique or the auto focusing technique.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A signal processing method comprising:
   receiving a signal obtained from an object as an input signal;
   generating a time lag signal from the input signal;
   calculating a difference between the input signal and the time lag signal; and
   detecting the generation of the difference so as to feature a portion of the object at a position where the difference is generated.

2. The signal processing method according to claim 1, further comprising removing noises from the input signal beforehand.

3. The signal processing method according to claim 2, further comprising, after receiving the input signal, carrying out AD conversion by sampling the input signals over a predetermined period,
   wherein the removing of noises from the input signal is carried out by leveling out a predetermined number of the sampled signals obtained sequentially from the A/D conversion.

4. The signal processing method according to claim 1, further comprising, after receiving the input signal, carrying out AD conversion by sampling the input signals over a predetermined period,
   wherein the time lag signal is generated by leveling out a predetermined number of the sampled signals obtained sequentially from the A/D conversion.

5. The signal processing method according to claim 1, further comprising removing spike noises from the input signal beforehand.

6. A signal processing method comprising:
   receiving a signal obtained from an object as an input signal;
   generating a first order time lag signal from the input signal;
   generating a second order time lag signal from the first order time lag signal;
   calculating a difference between the first order time lag signal and the second order time lag signal; and
   detecting the generation of the difference so as to feature a portion of the object at a position where the difference is generated.

7. The signal processing method according to claim 6, further comprising removing noises from the input signal beforehand.

8. The signal processing method according to claim 7, further comprising, after receiving the input signal, carrying out AD conversion by sampling the input signals over a predetermined period,
   wherein the removing of noises from the input signal is carried out by leveling out a predetermined number of the sampled signals obtained sequentially from the A/D conversion.

9. The signal processing method according to claim 6, further comprising, after receiving the input signal, carrying out AD conversion by sampling the input signals over a predetermined period,
   wherein the time lag signal is generated by leveling out a predetermined number of the sampled signals obtained sequentially from the A/D conversion.

10. The signal processing method according to claim 6, further comprising removing spike noises from the input signal beforehand.

11. A signal processing device comprising:
    an input part for inputting a signal obtained from an object as an input signal;
    a time lag signal generating part for generating a time lag signal from the input signal;
    a difference generating part for calculating a difference between the input signal and the time lag signal; and
    a featuring part for featuring a portion of the object at a position where the difference is generated by detecting the generation of the difference.

12. The signal processing device according to claim 11, further comprising a noise removing part for removing noises from the input signal beforehand.

13. The signal processing device according to claim 12, further comprising an AD converting part that samples the input signals over a predetermined period,
wherein the noise removing part levels out a predetermined number of the sampled signals obtained sequentially from the A/D converting part.

14. The signal processing device according to claim 11, further comprising an AD converting part that samples the input signals over a predetermined period,
wherein the time lag signal generating part levels out a predetermined number of the sampled signals obtained sequentially from the A/D converting part.

15. The signal processing method according to claim 11, further comprising a spike noise removing part for removing spike noises from the input signal beforehand.

16. A signal processing device comprising:
an input part for inputting a signal obtained from an object as an input signal;
a first order time lag signal generating part for generating a first order time lag signal from the input signal;
a second order time lag signal generating part for generating a second order time lag signal from the first order time lag signal;
a difference generating part for calculating a difference between the first order time lag signal and the second order time lag signal; and
a featuring part for featuring a portion of the object at a position where the difference is generated by detecting the generation of the difference.

17. The signal processing device according to claim 16, further comprising a noise removing part for removing noises from the input signal beforehand.

18. The signal processing device according to claim 17, further comprising an AD converting part that samples the input signals over a predetermined period,
wherein the noise removing part levels out a predetermined number of the sampled signals obtained sequentially from the A/D converting part.

19. The signal processing device according to claim 16, further comprising an AD converting part that samples the input signals over a predetermined period,
wherein the time lag signal generating part levels out a predetermined number of the sampled signals obtained sequentially from the A/D converting part.

20. The signal processing device according to claim 16, further comprising a spike noise removing part for removing spike noises from the input signal beforehand.

21. A signal processing device comprising:
a circuit module for inputting a signal obtained from an object as an input signal;
a circuit module for generating a time lag signal from the input signal;
a circuit module for calculating a difference between the input signal and the time lag signal; and
a circuit module for featuring a portion of the object at a position where the difference is generated by detecting the generation of the difference.

22. The signal processing device according to claim 21, further comprising a circuit module for removing noises from the input signal beforehand.

23. The signal processing device according to claim 22, further comprising an AD converting circuit module that samples the input signals over a predetermined period,
wherein the circuit module for removing noises from the input signal is a circuit module that levels out a predetermined number of the sampled signals obtained sequentially from the A/D converting circuit module.

24. The signal processing device according to claim 21, further comprising an AD converting circuit module that samples the input signals over a predetermined period,
wherein the circuit module for generating the time lag signal is a circuit module that levels out a predetermined number of the sampled signals obtained sequentially from the AID converting circuit module.

25. The signal processing method according to claim 21, further comprising a circuit module for removing spike noises from the input signal beforehand.

26. A signal processing device comprising:
a circuit module for inputting a signal obtained from an object as an input signal;
a circuit module for generating a first order time lag signal from the input signal;
a circuit module for generating a second order time lag signal from the first order time lag signal;
a circuit module for calculating a difference between the first order time lag signal and the second order time lag signal; and
a circuit module for featuring a portion of the object at a position where the difference is generated by detecting the generation of the difference.

27. The signal processing device according to claim 26, further comprising a circuit module for removing noises from the input signal beforehand.

28. The signal processing device according to claim 27, further comprising an AD converting circuit module that samples the input signals over a predetermined period,
wherein the circuit module for removing noises from the input signals is a circuit module that levels out a predetermined number of the sampled signals obtained sequentially from the A/D converting circuit module.

29. The signal processing device according to claim 26, further comprising an AD converting circuit module that samples the input signals over a predetermined period,
wherein the circuit module for generating a time lag signal levels out a predetermined number of the sampled signals obtained sequentially from the A/D converting circuit module.

30. The signal processing device according to claim 26, further comprising a circuit module for removing spike noises from the input signal beforehand.

* * * * *